United States Patent [19]
Williams, Jr.

[11] Patent Number: 5,520,282
[45] Date of Patent: May 28, 1996

[54] STRENGTHENED HANDLES IN MEMBRANOUS ARTICLES

[75] Inventor: James P. Williams, Jr., Thousand Oaks, Calif.

[73] Assignee: Devon Industries, Inc., Chatsworth, Calif.

[21] Appl. No.: 147,336

[22] Filed: Nov. 3, 1993

[51] Int. Cl.⁶ .................................................. B65D 1/34
[52] U.S. Cl. ........................ 206/370; 206/557; 220/771; 383/7
[58] Field of Search ................... 220/771; 206/557–564, 206/363, 370; 383/6, 7

[56] References Cited

U.S. PATENT DOCUMENTS

| | | |
|---|---|---|
| 4,865 | 4/1872 | Stuart . |
| 1,490,353 | 4/1924 | Wagemaker . |
| 3,442,378 | 5/1969 | Wolfe ........................................ 206/564 |
| 3,589,511 | 6/1971 | Britt ........................................... 206/558 |
| 3,697,223 | 10/1972 | Kovalick et al. . |
| 4,925,047 | 5/1990 | Valentine et al. . |
| 4,961,500 | 10/1990 | Coulombe ................................ 206/562 |
| 5,056,656 | 10/1991 | Pöll ........................................... 206/560 |
| 5,072,832 | 12/1991 | Valentine et al. . |
| 5,203,836 | 4/1993 | Brazis et al. ............................. 220/771 |

*Primary Examiner*—Stephen P. Garbe
*Attorney, Agent, or Firm*—Poms, Smith, Lande & Rose

[57] ABSTRACT

A novel manufacturing technique for strengthening integrally molded handles on a membranous or thin-film article against tearing, by integrally molding the peripheries of the handles and adjacent rim regions of the article in a mold which provides a three-dimensional curvilinear pre-bias against the stress-pattern engendered by lifting of masses carried by the article.

11 Claims, 1 Drawing Sheet

STRENGTHENED HANDLES IN MEMBRANOUS ARTICLES

FIELD OF THE INVENTION

This invention relates to articles manufactured of membranous or other flexible, pliable material or film, such as disposable surgical instrument cradles or devices for rejection of waste materials, and to a method of strengthening integrally-molded handles by means of which such articles may be lifted, without tearing of the handles, even when the article carries a significant mass contained within or appended to it.

BACKGROUND OF THE INVENTION

The present inventor has recently co-invented and the assignee is soon to market a disposable surgical instruments cradle, manufactured in one presently preferred embodiment of flexible, pliant, thin, membranous material referred to hereinafter for brevity as "film". This cradle and its novel features, including drainability provided by bottom porosity, are the subjects of a recently filed and presently copending patent application.

In experimenting with the most cost-effective manufacture of such an article, it was discovered that if the film is thin enough to keep the cost at a reasonable level for a disposable item (and, for environmental protection reasons, to keep the volume of this non biodegradable disposable item to a minimum), the film lacked sufficient strength, when manufactured in the most obvious manner, to keep the handles from tearing loose when the cradle was lifted carrying a full load of sterile solution and medical instruments deposited therein.

The present invention was discovered as a solution to the specific problem just mentioned; however, it is self-evidently of broader usefulness and wider applicability. In fact, the inventor is now considering applying this new methodology for handle-strengthening to the handles provided on other membranous articles manufactured by the present invention's assignee.

SUMMARY OF THE INVENTION

In accordance with the principles of the present invention, there is provided a novel technique for strengthening integrally molded handles on substantially membranous articles, by integrally molding the peripheries of the handles and adjacent rim regions of such articles in a mold which provides a three-dimensional curvilinear "pre-bias" against tearing. In the specification and claims hereinbelow, we shall use the term "bias" with only one of its several meanings, and therefore this term will now be defined more particularly as it is used hereinbelow.

According to *Webster's New Universal Unabridged Dictionary*, Second Edition (1979), a primary meaning of the transitive verb bias is "to warp", and a synonym of the noun "bias" is "bent" or "tendency". (In the English language, bias comes from a French noun for "slope" or "slant"; and in tailoring, "bias" means to cut or sew diagonally; however, the purpose of a bias cut is to produce a garment which fits "more smoothly" when stretched over a three-dimensional convex solid.)

By a "pre-bias" we shall mean hereinbelow a pre-molded or otherwise integrally formed three-dimensional curvilinear [i.e. non-planar] prepared or preformed warp in the membranous material under discussion. The purpose of this warp is to anticipate the manner in which the membranous material would be stretched if it had been molded flat and then handles made by the insertion of holes (either by integral molding or by cutting, punching or melting through a previously solid area), and then the material lifted by the handle or handles while having an additional significant weight contained by or attached to the material.

The present specification not only discloses the empirical efficacy of, but the specification provides a theoretical basis for the rational dynamical explanation of, the fact that by providing such warping, which provides extra material at locations where there would have been extra stretching if the material had been made flat before use, the tendency to tear is effectively removed. A more detailed technical exposition of this point will be found in another section below.

It is noted that the concept of pre-warping to minimize tearing is intuitive, and demonstrated empirically. After the actual reduction to practice, it was learned that there is an established theoretical principle (concerning "minimal-area surfaces" to "minimize surface tension energy") which can be used in hindsight to "explain" why the invention works, and which can be used to present the principles by means of which the invention can be systematically optimized. For the sake of efficient communication with those versed in Computer-Aided Engineering (CAE), these principles are included in the detailed explanation of the invention. However, no attempt has been made to remove these well-known principles from the public domain or to claim those principles as part of the present discovery and disclosure. Users of the present invention can "make and use without undue experimentation" by following the present inventor's original intuitive procedure. However, those inclined to make and use based on CAE with little or no experimentation may find the theoretical explanation of why the invention works to be of help; others may skip the theoretical details without thereby being deprived of an enabling disclosure.

In accordance with a further aspect of the invention, the peripheries of solid-area protrusions or flaps upon membranous material may be strengthened by the same method of manufacture, and then the flaps may be converted into handles by pre-molding, melting, cutting or punching holes in them.

Other objects, features, and advantages will become apparent from a consideration of the following detailed description and from the accompanying drawings.

DETAILED DESCRIPTION OF THE PRESENTLY PREFERRED EMBODIMENT

Figure 1:
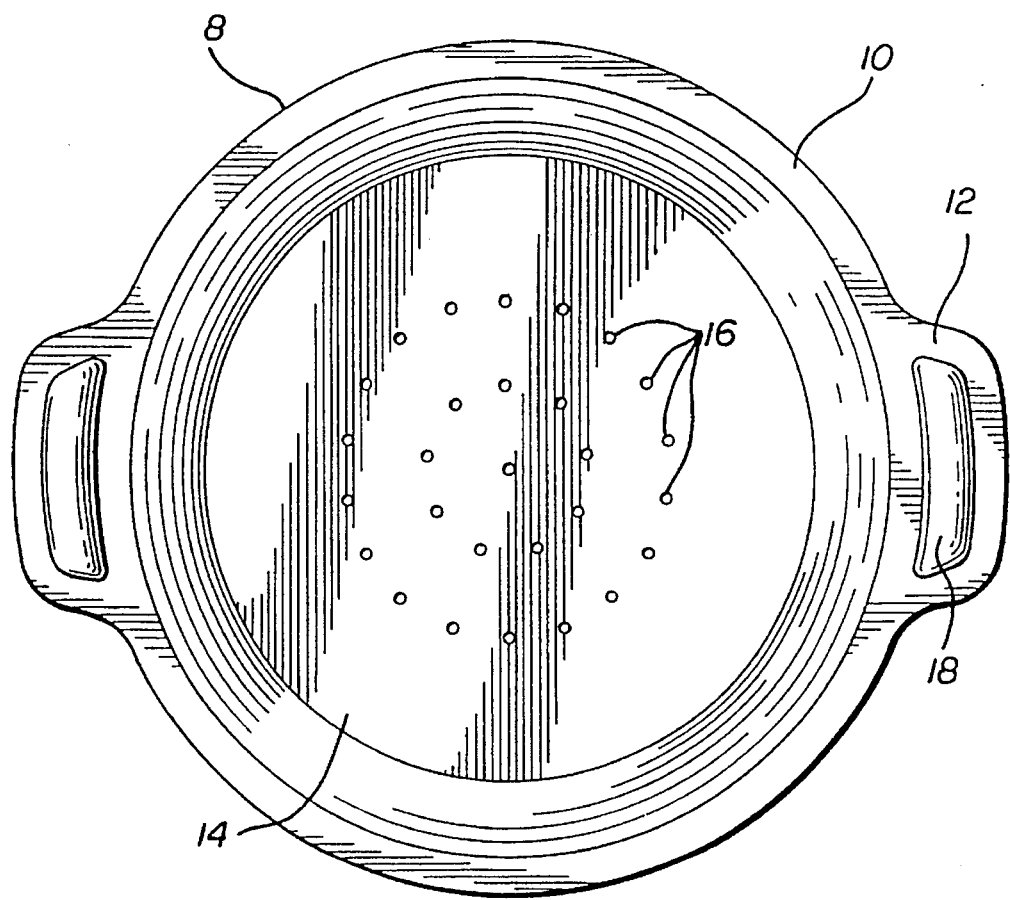
FIG. 1 is a horizontal planform of a surgical instruments cradle manufactured of flexible, pliable, membranous material and including a rim and handles as well as porosity elements.
Figure 2:
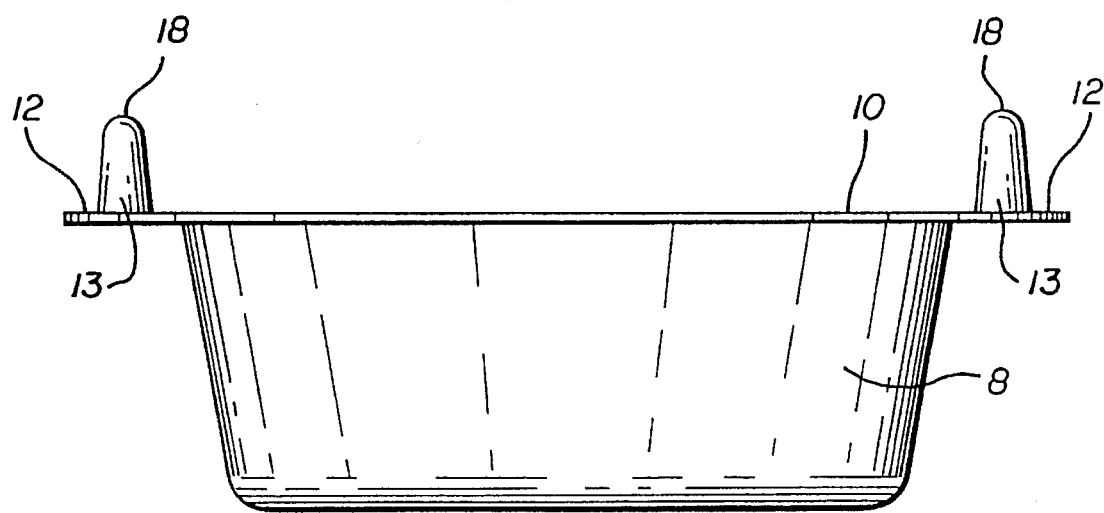
FIG. 2 is a cutaway vertical cross-section of the cradle of FIG. 1 depicting certain details of the three-dimensional curvilinear design and manufacture of the handles.

Referring to FIG. 1 and FIG. 2, a typical article of manufacture to which the presently disclosed invention may be provided is illustrated in both planform and cross-sectional views.

Substantially cylindrical membranous article 8, which is integrally molded of a synthetic polymer, and may have porosity elements (or holes) 16 in its bottom 14 (in this particular example, but not in general) has a rim 10 from which ear-like protrusions or flaps 12 protrude. The flaps may be made into handles by the provision of apertures 18 in the flaps 12 which facilitate manual lifting.

The bilateral symmetry created by placement of the flaps 12 in extensions of the rim 10 on diametrically opposite sides of the periphery of the rim 10 enables the article 8 to be lifted manually with approximately equal stress placed upon each flap.

If the handles are made flat, they will often lack sufficient strength not to tear when a full load is lifted within or appended to the article 8. This problem can be eliminated by providing a three-dimensional curvilinear bias in the material adjacent to and within the handle, as depicted in FIG. 2, wherein the empty gap or hollow 13 is created in the flaps 12 by means of appropriate three-dimensional molding procedures. In fact, the mold which creates the article 8 by integral molding is formed as a two-tiered structure (not shown), the bottom tier of which is adapted to configure the substantially cylindrical portion of the article 8, while the upper tier is adapted to configure the handle-bearing protrusions 12 as flaps surrounding the hollows 13 at chosen diametrically opposite locations on the rim 10. This pre-biased nature of the pliant material or film of which the article 8 is molded is selected to reduce any additional tendency to stretch the material during the stress pattern engendered by the lifting of significant masses contained within or appended to the article 8.

This novel method of pre-biasing the peripheries of a handle (or area which will become a handle) is in contrast to the obvious or simplistic procedure for manufacturing an article of this type, in which the membranous material comprising the region of interest is manufactured either substantially "flat" (in the sense that the region could be placed in contact with a region of a plane surface without significant stretching), or else substantially "flattenable" (in the sense that the region can be so placed after being unrolled, i.e. after being stretched or compressed at each point in only a single direction, and not stretched at all in at least one direction which is perpendicular to that direction).

For CAE-users: more specifically, as defined in differential geometry, consider the Gaussian curvature K of a two-dimensional smooth (differentiable) surface. It is well-known that $K=\kappa_1 \cdot \kappa_2$, namely the Gaussian curvature is the product of the two principal curvatures $\kappa_i$, (i=1, 2), where it can be proved that at any point on the surface there are always two "best fitting" or osculating three-dimensional circles, lying in planes perpendicular to each other at the point in question, the reciprocals of whose radii $R_i=1/\kappa_i$, (i=1, 2), define the "principal" curvatures. By a region of a surface which is flat one means a region of the surface upon which it is true that K=0 because both principal curvatures are identically zero; and by a region which is flattenable we shall mean hereinbelow a region upon which it is true that the Gaussian curvature vanishes identically because at least one of the principal curvatures is identically zero over the entire region [specifically, either $\kappa_1=0$ or else $\kappa_2\equiv 0$], while at the same time $(\kappa_1)^2+(\kappa_2)^2 \neq 0$ is allowed.

The solution to the problem of prevention of tearing of handles in flattenable membranous surfaces is to prepare with a suitable warp, or to "pre-bias", the surface at the peripheries of such handles, i.e. to MANUFACTURE the surface with $K \neq 0$ on such peripheral regions. Admittedly, the preceding differential-geometric characterization is merely a necessary and not a sufficient condition for the accomplishment of the objective of the present invention.

There is no uniquely sufficient condition for the accomplishment of the objective of the present invention, because the invention works when the objective is attained merely adequately to prevent tearing, and no requirement that this prevention should be obtained with optimality is imposed. Indeed, there is no uniquely definable "optimal" solution to this problem, as the following theoretical discussion will illustrate.

To solve the problem with "optimality" one needs to define the outer extent of the "periphery" of the handles, but this can be done in various arbitrary ways.

For simplicity, we shall first consider the problem of optimizing the CAE design of a solid-area flap, and later return to the problem of optimizing the design of a flap which is to have a hole made in it.

So consider now the simplified CAE problem of minimizing the integrated stress-energy (or "total stretching energy") on a flap which is imagined to be lifted by grasping it on both sides simultaneously, i.e. to be lifted while experiencing (as an idealization) a constant surface tension throughout the surface area of the flap.

The most obvious way to design the boundary is to move outward from interior of the flap, and through the warped handle region toward the region where the flap joins the remainder of the membranous article, until one encounters a portion of the membranous article's surface which it is acceptable to leave in the originally flattenable condition. This can be done conceptually by taking a thin wire hoop or circle and bending it in three dimensions until it defines the outer boundary of the region in question. (Since there is no unique way to do this, there is no unique way to solve the problem at hand; but ANY allowable way is acceptable.) Now the problem of designing the surface within that boundary so as to minimize the integrated total stress-energy produced by the stretching of that surface is a variant of a famous problem in the Calculus of Variations called "Plateau's Problem".

An intuitive understanding of Plateau's Problem can be obtained by simply regarding it as the "three-dimensional isoperimetric minimal surface area" or "soap-bubble-film problem", i.e. given the fixed wire hoop (or boundary curve $\Gamma$), dip it into a container of soap-bubble solution, and, by withdrawing it, stretch a film of soap-bubble material so that its boundaries are precisely coincident with the three-dimensional closed curve $\Gamma$ defined by the wire; i.e. find the surface $\Sigma$ of minimal area $S \equiv | \Sigma |$ whose fixed boundary $\Gamma$ is the given bent wire-hoop. Because a soap-bubble-film is presumed to have constant surface tension $\sigma$, the solution to the problem of minimal area also solves the problem of minimizing the total stretching energy W on the stressed area S (which is just the minimized area S multiplied by the surface tension $\sigma$, i.e. $W=\sigma \cdot S$).

Plateau's Problem is an example of a rather difficult class of problems in the Calculus of Variations which were not solved until the 1930's (by the American mathematician Jesse Douglas). Analytically the solution is very elegant, namely a surface $\Sigma$ is a minimal surface if and only if its principal curvatures $\kappa_i$, (i=1, 2), everywhere satisfy the relationship $$\kappa_1+\kappa_2 \equiv 0.$$

This means that (if both curvatures are non-zero) then the curvatures have opposite sign, i.e. the surface is everywhere hyperbolic [like a saddle-surface] in that its two principal osculating circles at each point are tangent to the surface from opposite sides (i.e. lie on opposite sides of the [planar]

tangent surface to $\Sigma$ at the same point). The preceding expression is called the mean curvature and the condition that the mean curvature must vanish is a well-known necessary condition for a surface to be a minimal surface (as proved, for example, in the standard physics text of Joos cited hereinbelow).

The same solution applies to minimal surfaces with disconnected boundaries, e.g. two separate boundary curves $\Gamma_1$ and $\Gamma_2$, as in the more realistic or complete version of the problem at hand, in which now the second boundary curve represents the perimeter of the hole which is to be made in the flap. Using the notation of algebraic topology, we say that the union of the two disjoint curves $\Gamma_1$ and $\Gamma_2$ constitutes the boundary of the surface $\Sigma$ by writing $$\partial\Sigma=\Gamma=\Gamma_1 \cup \Gamma_2.$$

Now the problem can be re-stated just as before: we desire to minimize $S\equiv|\Sigma|$, given the boundary $\Gamma=\partial\Sigma=\Gamma_1 \cup \Gamma_2$, and this problem has the same analytical solution already presented.

The preceding theoretical discussion is not novel but is familiar to those versed in the subject of CAE as related to "surface tension in liquids". For an expository derivation from first principles, consult pages 222–227, incorporated herein by reference, of the standard undergraduate text *Theoretical Physics* by G. Joos, Third Edition, Dover Publications Inc., New York, 1986. In particular note the concluding sentences of this reference: "Surfaces for which the [mean curvature] vanishes are called minimal surfaces, since they are the surfaces of smallest area for a given boundary curve. It is at once evident that a stretched skin, corresponding as it does to a liquid film, assumes a form having a minimum area." [Emphases added.]

With this theoretical understanding in hand (or accepted as well-established in this art), and given any pair of non-planar closed boundary curves $\Gamma_1$ and $\Gamma_2$, it is not difficult to conjecture intuitively the approximately optimal shape of the corresponding minimal surface $\Sigma$; this is why it is not always necessary to do a numerical CAE solution of this problem in order to arrive at satisfactory results by a combination of "educated intuition" plus a very limited application of the trial-and-error approach.

Of course it is possible to solve this "optimal CAE design" problem with greater precision, if so desired. Today's digital computers can find an arbitrarily close numerical approximation to the solution of problems in this category by various means, called Direct Methods in the Calculus of Variations, such as the Rayleigh-Ritz-Galerkin Method, and including the CAE engineering technique (for which commercial program "toolkits" are available) called the Finite Element Method (FEM).

If it were of sufficient economic importance to justify such a complete Stress Engineering Analysis solution, the preceding techniques could be employed to find an "optimal" solution to the design of the required "pre-bias" design. However, the present inventor has found in practice so far that without undue experimentation, or employment of sophisticated CAE engineering analysis techniques, an acceptably adequate solution to the "pre-bias" design problem can be attained by a combination of intuition and a limited amount of trial-and-error experimentation.

For the benefit of any proposed user of the method disclosed hereinabove who feels that the preceding partly "intuitive" solution requires "undue" experimentation, the present inventor notes that the precisely "optimal" CAE solution can ALWAYS be obtained (by numerical solution of Plateau's Problem for the case at hand) in a perfectly systematic way, with no experimentation whatsoever. Accordingly, up to the slight arbitrariness in selection of the three-dimensional closed curves $\Gamma_1$ and $\Gamma_2$ defining the boundaries of the handle's periphery, the well-known theoretical methodology cited hereinabove for expository purposes is precisely well-defined in terms of its capability to be used to specify an OPTIMAL embodiment $\Sigma$, and it is a well-established principle of practical engineering that in order to enjoy the advantages of an improvement, one does not need to go to the trouble and expense to make an exceedingly close approach to the optimal embodiment, rather one makes a "trade-off" between cost-effectiveness of a close approach to the ultimate and an intuitively-obtained, merely adequate approach to the ultimate. The statement by the present inventor that a merely adequate approach to the theoretical optimal defined hereinabove has sufficed for his presently preferred embodiments does not preclude any user of the public-domain theoretical CAE methodology, cited and recalled hereinabove, from approaching as close to the theoretically exact optimal embodiment as the requirements of the particular case at hand may dictate.

RAMIFICATIONS, SCOPE AND CONCLUSION

In conclusion, it is to be understood that the foregoing detailed description, and the accompanying drawings relate to but one presently preferred illustrative embodiment of the invention. However, various changes may be made without departing from the spirit and the scope of the invention.

Thus it is possible to select any desired trade-off between expense of design and cost of product in deciding whether or not to do a complete CAE engineering analysis and to minimize the integrated stress-energy by employment of the direct method of the calculus of variations as applied to an example of Plateau's Problem in the differential geometry of three-dimensional configurations of two-dimensional surfaces $\Sigma$ bounded by three-dimensional curves $\Gamma_1$ and $\Gamma_2$ [i.e. to minimize $S\equiv|\Sigma|$, given the boundary $\partial\Sigma=\Gamma_1\cup\Gamma_2$], or to accept any rough approximation to the well-defined optimal solution $\Sigma$ as long as the practical results are acceptable for the case at hand.

Also, it is possible to use composite materials to fabricate the article 8 instead of integral molding of synthetic polymers such as the presently preferred thermoplastic polyolefin resin materials. In addition, the parts (i.e. rim 10 [if any], flaps 12, floor 14 [if any], and handle-aperture 18 need not have the precise configuration described hereinabove, but may have alternative arrangements.

Accordingly, it is to be understood that the detailed description and the accompanying drawings as set forth hereinabove are not intended to limit the breadth of the present invention, which should be inferred only from the following claims and their appropriately construed legal equivalents, rather than from the examples given.

What is claimed is:

1. A storage device, comprising:
   a storage portion composed of a thin, substantially flexible film and defining a storage area therewithin and an upper edge; and
   at least one handle associated with the upper edge, the at least one handle being composed of the thin, substantially flexible film and including a pre-biased area defining a three-dimensional curvilinear shape which reduces any additional tendency to stretch the thin, substantially flexible film during the stress pattern engendered by lifting the storage device with a significant mass stored in the storage portion.

2. A storage device as claimed in claim 1, wherein the storage area, upper edge and handle are integrally formed.

3. A storage device as claimed in claim 1, wherein the thin, substantially flexible film comprises a thermoplastic polyolefin resin material.

4. A storage device as claimed in claim 1, wherein the at least one handle comprises a pair of handles.

5. A storage device as claimed in claim 1, wherein the at least one handle defines an open end and a closed end.

6. A surgical instrument cradle, comprising:

a storage portion composed of a thin, substantially flexible film and defining a storage area therewithin, a bottom portion and an upper edge, the bottom portion defining a plurality of porosity elements; and at least one handle associated with the upper edge, the at least one handle being composed of the thin, substantially flexible film and including a pre-biased area defining a three-dimensional curvilinear shape.

7. A surgical instruments cradle as claimed in claim 6, wherein the three-dimensional curvilinear shape defines a shape which reduces any additional tendency to stretch the thin, substantially flexible film during the stress pattern engendered by lifting the storage device with a significant mass stored in the storage portion.

8. A surgical instruments cradle as claimed in claim 6, wherein the storage area, upper edge and handle are integrally formed.

9. A surgical instruments cradle as claimed in claim 6, wherein the thin, substantially flexible film comprises a thermoplastic polyolefin resin material.

10. A surgical instruments cradle as claimed in claim 6, wherein the at least one handle comprises a pair of diametrically opposed handles.

11. A surgical instruments cradle as claimed in claim 6, wherein the at least one handle defines an open end and a closed end.

* * * * *